United States Patent
Shen et al.

(10) Patent No.: US 7,255,559 B2
(45) Date of Patent: Aug. 14, 2007

(54) DISPOSABLE DENTAL PROPHY ANGLE WITH SECURE RETENTION MECHANISM

(75) Inventors: Jianping Shen, Los Angeles, CA (US); Daniel Wang, Rowland Heights, CA (US)

(73) Assignee: PAC-DENT International, Inc., Walnut, CA (US)

( * ) Notice: Subject to any disclaimer, the term of this patent is extended or adjusted under 35 U.S.C. 154(b) by 263 days.

(21) Appl. No.: 10/929,225

(22) Filed: Aug. 30, 2004

(65) Prior Publication Data

US 2006/0046227 A1    Mar. 2, 2006

(51) Int. Cl.
*A61C 3/06* (2006.01)

(52) U.S. Cl. .................. 433/125; 433/118; 433/166

(58) Field of Classification Search ................ 433/125, 433/114, 118, 122, 166
See application file for complete search history.

(56) References Cited

U.S. PATENT DOCUMENTS 6,053,732 A * 4/2000 Sale ........................... 433/125

2004/0014004 A1 * 1/2004 Garrison et al. ............ 433/125

\* cited by examiner

*Primary Examiner*—Cris Rodriguez
*Assistant Examiner*—Candice C. Stokes
(74) *Attorney, Agent, or Firm*—Bo-In Lin

(57) ABSTRACT

A disposable, securely retained dental angle is provided. The angle includes a one-piece hollow housing having a short leg at its front end, which is angled with respect to the long leg. Both the short and long legs have a through bore. The short leg has an aperture, which is connected to the bore of the long leg to allow insertion of a driving shaft through the short leg of the angle. A driven rotor is inserted in the short leg. A horse-shoe-like snap rotor retainer fits within the short leg over the driven rotor to retain the driven rotor in the angle. A paw-like or, alternately, a horse-shoe-like locking means fits within the long leg over the driving shaft to lock the driving shaft in the angle and to retain the angle together. In one embodiment, a pair of splinters on the driven rotor provides the function to retain the rubber prophy cup firmly while the driven rotor is in operation.

15 Claims, 4 Drawing Sheets

DISPOSABLE DENTAL PROPHY ANGLE WITH SECURE RETENTION MECHANISM

FIELD OF THE INVENTION

The present invention relates to a disposable dental appliance and more particularly to a dental prophylaxis angle (or "prophy angle") used for cleaning and polishing teeth, especially to the prophylaxis angle for holding a disposable polishing/cleaning cup-head that is disposed after each application to a patient to prevent potential cross infections.

BACKGROUND OF THE INVENTION

A prophy angle is a dental appliance employed by a dentist or dental hygienist in a dental treatment to remove the plaque and polish the surface of the dentin of teeth. A prophy angle includes a prophy cup that is secured to the angle and is rotated by a drive mechanism, typically a gear drive. The prophy cup is shaped to retain a desired amount of prophy paste, which is used to polish and clean a patient's teeth.

In order to rotate a prophy cup to perform the teeth cleaning and polishing task, a dental prophy angle includes a driving mechanism that is typically implemented with a gear connection between a driving gear shaft and a driven gear rotor with a right angle. The driving rotor is rotated by a dental handpiece with a speed of about 2,000 to 5,000 rpm, then the rotation is transferred to the driven rotor by the gearing mechanism resulting in rotating the attached prophy cup at a right angle.

However, since the prophy angle includes the moving parts connected by driving gears while the gear connections and the prophy cup are continuously operated with high speed rotation, the long term reliability and consistent performance of the gear connection and the rotational prophy cup become a technical challenge. Poor long-term reliability often becomes a problem, particularly for the components made of plastic. The plastic components may be implemented either as moving parts or as part of the gear connections between the moving parts and these plastic components often cracks or break off when subject to tearing forces if these the moving parts or the gear connections are not tightly engaged. In order to improve the reliability by reducing the material wear and degradation under constant use and to eliminate potential weak links, many patented inventions have been disclosed. These disclosures provide new gear material, gear shape, gear position and novel lubrications. These previous patents include U.S. Pat. Nos. 6,203,322, 5,964,590, 5,749,728, 5,730,595, 5,645,426, 5,120,220, and 5,040,978. However, in the present market, many of the prophy angle products still exhibit operating life problem because of the insecure gearing connection, which leads to unreliable performance and causes inconvenience for dentists and hygienists Therefore, a need still exists in the art of designing, component manufacturing and assembling the prophy angles to provide new and improved configuration implemented with better engagement contacts between the moving components to enable a more secure retaining of the driving shaft and driven rotor to assure reliable and high performance operations of a prophy angle.

SUMMARY OF THE PRESENT INVENTION

It is therefore an object of the present invention to provide a new and improved design and configuration to securely maintain the lateral positions of the driving shaft and the driven rotor such that tight engagements between the driving shaft and driven rotor can be continuously maintained. By minimizing lateral shifts and maintaining tight engagement between the rotating gears, unnecessary wears and damages caused by unreliable gear engagement can be reduced. Secure retaining of the driven rotor and the prophy cup further improve the convenience of operation to allow better performance in patient treatments. The above-mentioned problems and difficulties are therefore resolved.

In order to accomplish the object of secure connection, the present invention provides a secured horse-shoe-shaped driven-gear-retainer which retains the neck of the driven gear so as to secure the head portion of the driven-gear member in position, as well as a secured driving shaft locking element to ensure the driving gear is engaged to the driven gear properly during operating.

Specifically, the invention is directed to a dental prophy angle that has an integrally formed housing, which incorporates two gears (driving gear and driven gear) with a removable prophylaxis head attachment, also called the prophylaxis cup (or "prophy cup"), and translates rotation from a dental power source to the head attachment through both driving and driven gears. More specifically, the driving gear rotor, which receives the dental power source on one end and engages with the driven gear on the other end, translates the rotation to the driven gear rotor in an angled axis. The angle is made of inexpensive plastic and can be discarded after each treatment, thus preventing cross-infection and reducing the expense and inconvenience of sterilization as well.

One aspect of the invention is the two gears are engaged perpendicular to each other on their inner sides of contact, instead of their outer sides, so that the rotation direction of the prophy cup will be the same, instead of opposite, as that of the driving gear and of other dental treatment devices connected with the driving gear. The consistency in rotation direction makes practitioners feel more comfortable.

Another aspect of prominent benefit of the present invention lies in the mating of the gears. Due to the existence of necessary operating tolerance, as the prophy angle operates the inner-contact-engagement makes the mating of gears closer when the driven gear rotor is pressed toward to the driving gear rotor by the force from the prophy cup. Contrarily, if the engagement uses the outer-side-contact, that arrangement will reduce the mating area when the driven gear rotor is pressed away from the driving gear rotor by the prophy cup as the prophy angle operates.

A further aspect of the invention is that the horse-shoe-shaped driven-gear-retainer is arranged in the short leg of the housing by retaining the neck of the driven gear to secure the head portion of the driven-gear member in position. Because of the inner-contact-engagement, a retaining mechanism is always adopted to prevent the driven gear rotor from falling out of the housing during operation. The arrangement of the horse-shoe-shaped driven-gear-retainer in this invention provides a secure means for retaining the prophy cup member from falling out of the passageway and keeping the prophy cup member rotating freely without much friction simultaneously. The inner-side contact gearing arrangement tends to eject the prophy cup-rotating member from the housing because the gear on the driving shaft applies an outward force to the rotating driven gear. Thus, the reliability of the driven-gear-retainer is an important aspect of the present invention. The horse-shoe-shaped driven-gear-retainer ensures in a simple way that the driven-gear rotor remains in position securely with much less cost in comparison with other similar products in market.

Yet another aspect of the invention is a secured driving shaft locking mechanism to ensure the driving gear is engaged to the driven gear properly without being pushed out during operation. Specifically, in the present invention, a paw-like disc with a several of axially aligned slots forming a locking positioner is placed in the long leg of the housing. The driving gear tail passes through the central hole of the locking positioner, so that when the locking positioner is snapped on the inside wall of the housing it will be held strongly at the exact position, to secure the driving-gear member axially in position. Rather than a plastic positioner, a metal one can better grasp the plastic housing. Preferably, a washer can be interposed between the retaining lock and the shoulder on the driving gear member to increase stability and reduce friction.

As an alternative to the paw-like disc type shaft locking mechanism in the present invention, a horse-shoe-like positioner is held firmly on the inside wall of the housing, with the driving gear tail passing through its fork-like legs, so as to secure the driving-gear member axially in position.

The last aspect of the present invention is directed to a pair of, or more, sharp pointed splinters arranged circumferentially on, and pointing outward from the neck of the cup end of the driven gear rotor, upon which the snap-on prophy cup sits. After the prophy cup is attached, the base of the prophy cup is pierced and thus securely anchored by the splinters arising from the neck of the driven gear rotor. These splinters pierce the rubber base of the snap-on prophy cup and force it to rotate with the driven gear rotator, eliminating the free spinning of the rotor within the cavity of the snap-on prophy cup.

These and other objects and advantages of the present invention will no doubt become obvious to those of ordinary skill in the art after having read the following detailed description of the preferred embodiment, which is illustrated in the various drawing figures. Other details and features of the invention will become apparent and described hereinafter with the following drawings.

BRIEF DESCRIPTION OF THE DRAWINGS

The features and advantages of the invention will be readily apparent from the following detailed description. The detailed description will be better understood in relation to the accompanying drawings as.

DETAILED DESCRIPTION OF THE INVENTION

Figure 1:
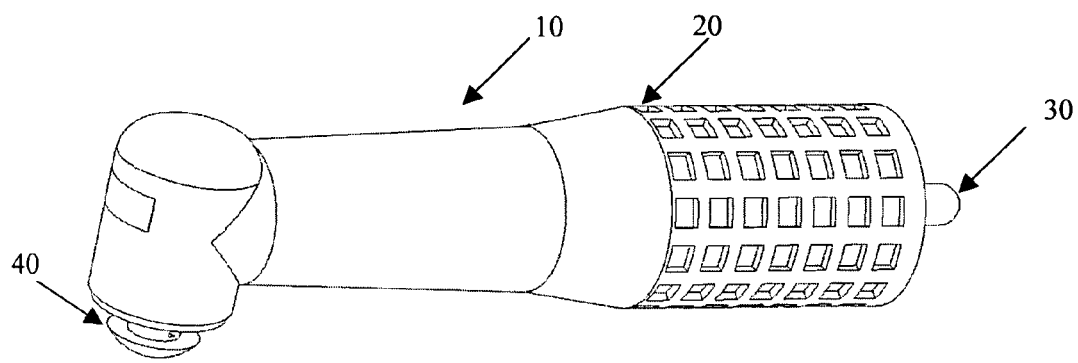
FIG. 1 shows the perspective view of the assembled prophy angle.

Referring first to FIG. 1 for a perspective view of a prophy angle 10 as a preferred embodiment of present invention. The prophy angle includes a driving shaft 30 that engages and driving a driven rotor 40. The prophy angle includes a long leg and a short leg wherein the driving shaft 30 extends along a longitudinal direction inside the long leg of the housing 20 and the rotator 40 extends along a perpendicular direction inside the short leg of the prophy housing 20. A powered dental handpiece (not shown) is provided to couple to the tail of the driving shaft 30 to rotate the shaft 30 and a snap-on rubber prophy cup with prophy paste (not shown) is provided to connect to the cup holder head of the driven rotor for rotate with the rotator 40 when driven by the rotating shaft 30.

Figure 2A:
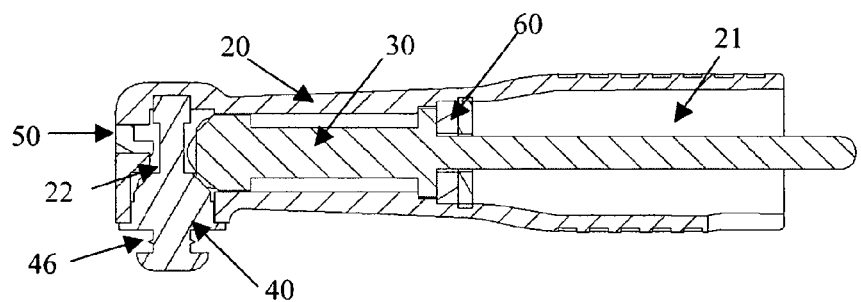
FIGS. 2A and 2B are cross sectional views of a prophy angle with a paw-like positioner and a horse-shoe-like positioner respectively.
Figure 2B:
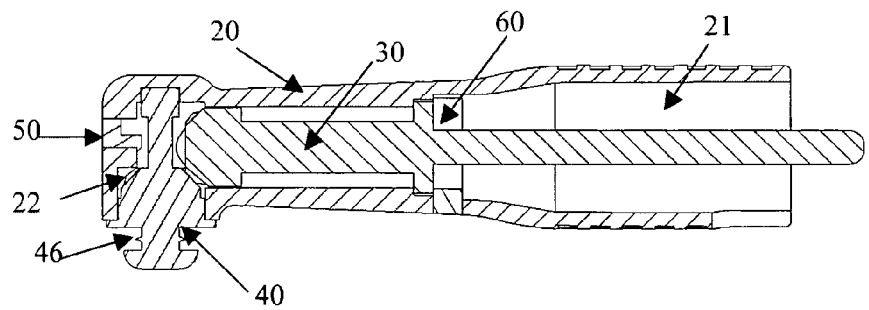

FIG. 2A is a cross-sectional view of the prophy angle shown in FIG. 1, where a driving rotating shaft 30 is enclosed in the housing 20. FIG. 2A represents the paw-like driving shaft positioner structure while FIG. 2B represents the horse-shoe-like driving shaft positioner structure. The prophy angle 20 further includes a driving shaft locking means 60 to retain the driving shaft at a fixed horizontal location. The driving shaft 30 is engages a driven rotator 40 to translate first rotation of the driving shaft 30 along a horizontal rotational axis to a second rotation of the driven rotor along a vertical rotational axis. The driven rotator 40 is maintained in a vertical position by a driven rotor retainer 50. At the lower end of the driven rotator 40, a pair of splinter is further provided to more securely attached to a disposable prophy cup (not shown) that is snapped onto the lower end of the rotor 40. The details structure of the driving shaft locking means 60 and the driven rotator retainer 50 will be further described below.

Figure 3A:
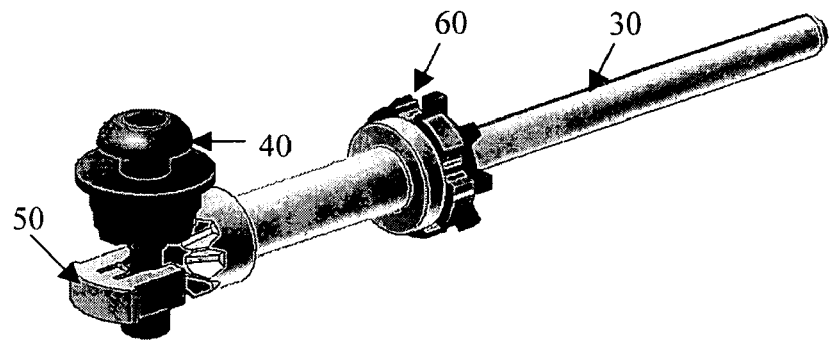
FIGS. 3A and 3B are perspective views of the assembled driving shaft and driven rotor for placement inside a housing with a paw-like positioner and a horse-shoe-like positioner respectively.
Figure 3B:
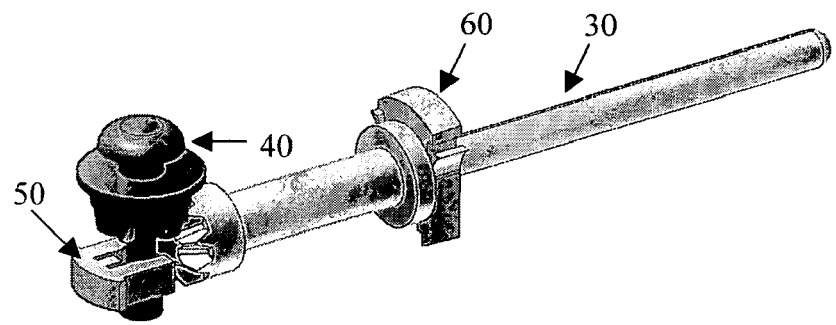

FIGS. 3A and 3B are a perspective views of the parts assembled inside housing for a paw-like driving shaft positioner structure and a horse-shoe-like driving shaft positioner structure respectively. In order to enclose the driving shaft 30 and the driven rotor inside the housing 20, the housing 20 has a hollow space as that shown in FIG. 2A or 2B. The housing 20 is hollow to provide a longitudinal passageway 21 and a transverse passageway 22 inside the short and long legs of the housing such that the driving shaft 30 and the driven rotor can be placed therein to engage each other for generating a gear-driving mechanism. The driving shaft 30 is placed along the longitudinal passageway 21 with a locking system 60 are preferably perpendicular to the transverse passageway 22 for placing the driven rotor 40 with the vertical position fixed by a driven rotor retainer 50 along the transverse passage 22.

Figure 4:
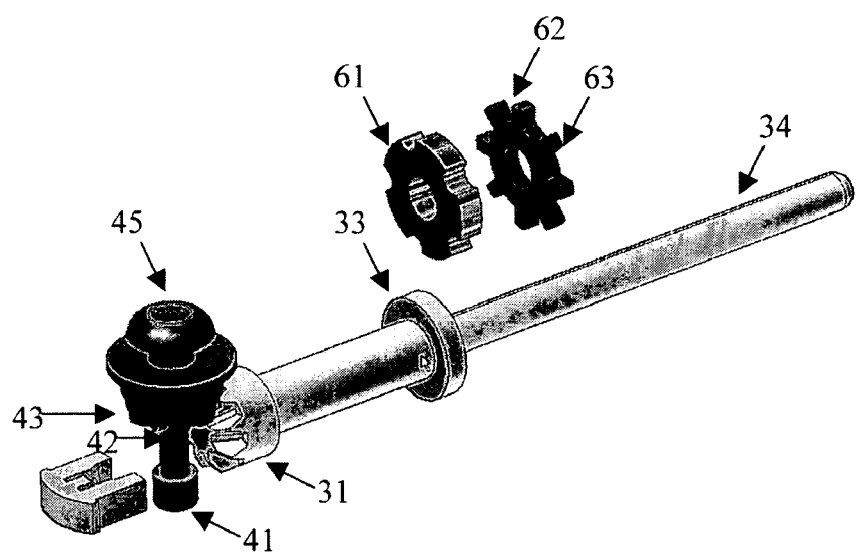
FIG. 4 is a perspective view of the parts inside the housing implemented with paw-like positioner before assembly.
Figure 5:
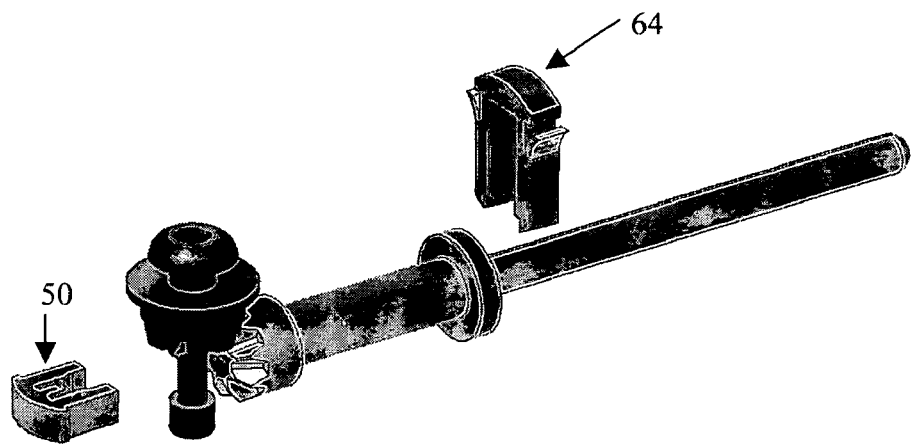
FIG. 5 is a perspective view of the parts inside the housing implemented with horse-shoe-like positioner before assembly.

It is desirable to fix driven rotor 40 with respect to driving shaft 30 to ensure constant gearing action during operation. At the near end of transverse passageway 22 of housing 20, there exists a driven rotor-positioning hole 23 centered on the axis of transverse passageway 22. The diameter of driven rotor positioning hole 23 is loosely fit to the diameter of rotor head 41 as shown in FIGS. 4 and 5 below of driven rotor 40 to ensure the concentricity of rotation of driven rotor 40. The depth of driven rotor positioning hole 23 is designed such that the gearing action between gear head 31 of driving shaft 30 and gear shoulder 43 of driven rotor 40 stays constant during rotation, and such that cup flange 44 stays slightly in contact with open end 29 of housing 20.

In order to prevent axial movement of driving shaft 30 from its position relative to driven rotor 40 within longitudinal passageway 21 of housing 20, there exist two longitudinal positioning steps 25, 26 on the wall of longitudinal passageway 21 of housing 20. The longitudinal positioning step 25 controls the axially forward position of driving shaft 30 by blocking the head side of shaft shoulder 33 in position when axially forward directed forces are exerted on driving shaft 30. Longitudinal positioning step two 26 positions driving shaft locking means 60 which controls the axially backward position of driving shaft 30 by blocking the tail side of shaft shoulder 33 in position when axially backward directed forces are exerted on driving shaft 30. There are slots 27 and 28 provided on the housing 20 for adapting the driving shaft locking means 60 as will be further described below.

Figures 6A, 6B:
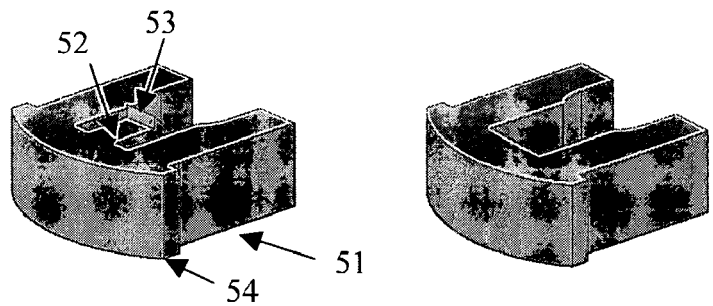
FIGS. 6A and 6B are perspective views of a driven-rotor-retainer for positioning the driven rotor at a fixed position, showing top and bottom views respectively.
Figure 6C:
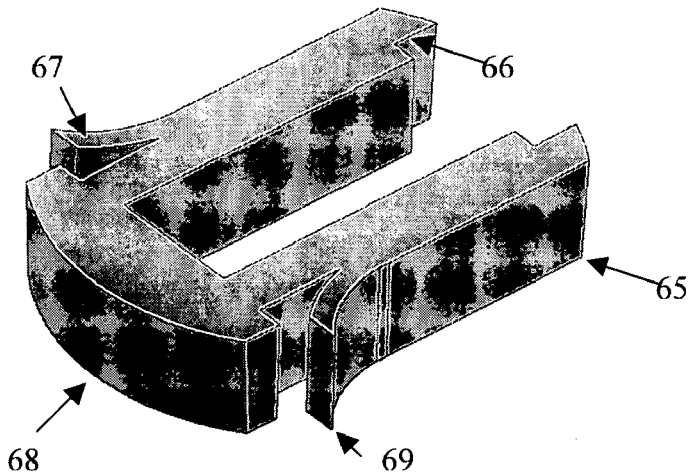
FIG. 6C is a perspective view of a horse-shoe-like positioner for locking the driving shaft at a fixed position.

FIGS. 4 and 5 are perspective views of the parts of FIGS. 3A and 3B respectively before these parts are assembled for showing the details of paw-like and horse-shoe-like positioners, respectively, e.g., the structural details of the driving shaft locking means 60 and the driven rotor retainer 50. Two kinds of retaining mechanism are presented for this invention to achieve the retaining function of driving shaft locking means 60: the paw-like mechanism as shown in FIG. 3A and FIG. 5, and the horse-shoe-like mechanism as shown in FIG. 3B and FIG. 6.

Referring to FIG. 4, the driving shaft locking means 60 includes a washer 61 and paw-like positioner 62. The head side of washer 61 is blocked by longitudinal positioning step 26 of longitudinal passageway 21 of housing 20 after final assembly. The diameter of washer 61 is slightly greater than the diameter of longitudinal positioning step 26 of longitudinal passageway 21 of housing 20 so that, after assembly, washer 61 provides an axially forward directed retaining force to driving shaft 30. Paw-like positioner 62 tightly presses the tail side of washer 61 after final assembly. The diameter of paw-like positioner is slightly greater than the diameter of longitudinal positioning step 26 of longitudinal passageway 21 of housing 20 so that, after assembly, paw-like retainer 62 provides an extra axially forward directed retaining force to driving shaft 30. Paw-like positioner 62 may be made of a metal material, retainer toes 63 are bent backwards and splintered into the wall of housing 20 to provide a strong axially backward directed retaining force during operation of prophy angle 10.

Figure 7A:
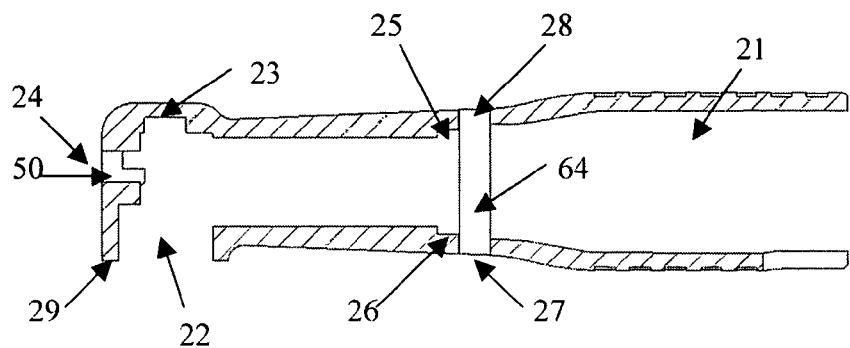
FIG. 7A is a cross-sectional view of a housing with horse-shoe-like positioner on for enclosing the gears.
Figure 7B:
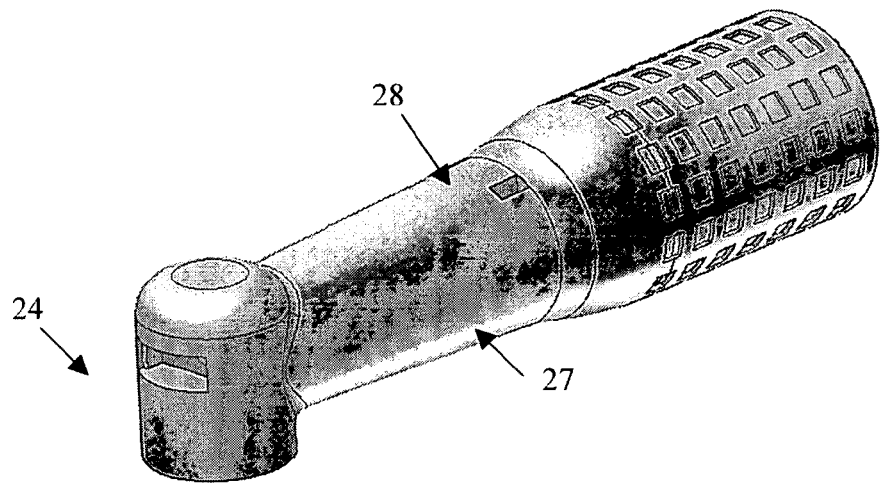
FIGS. 7B and 7C show a top perspective view and a bottom perspective view of the housing for enclosing the horse-shoe-like positioner and the horse-shoe-like retainer.
Figure 7C:
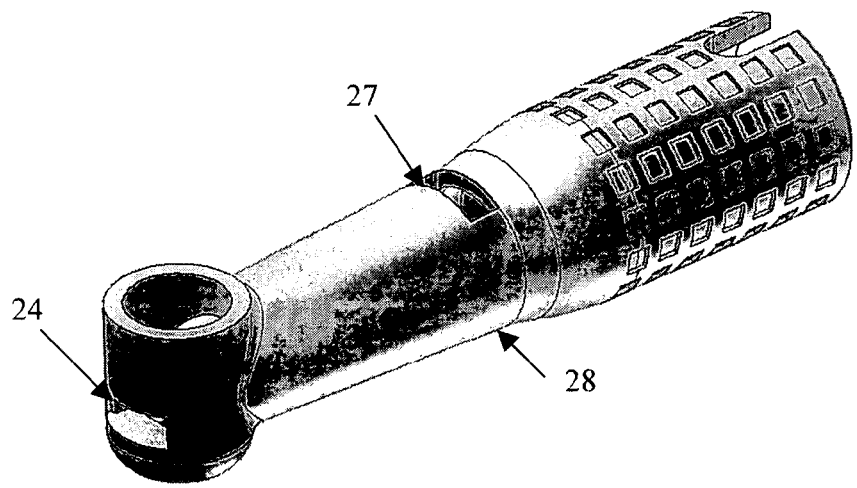

Referring to FIG. 5 for an alternate driving shaft locking means 60 that is simply made up by a horse-shoe-like locker 64. The detail structural features of the horseshoe locker 84 is further illustrated in FIG. 6B. The horse-shoe-like locker 64 is inserted through horse-shoe-like locker head slot 27 on the wall of longitudinal passageway 21 of housing 20 and reaches to horse-shoe-like locker tail slot 28 on the other side of the wall of longitudinal passageway 21 of housing 20. The front side of horse-shoe-like locker 64 is located at longitudinal positioning step 26 of longitudinal passageway 21 of housing 20 after assembly, and the horse-shoe-like locking means provides a strong longitudinal backward directed retaining force during operation of prophy angle 10. Transverse locking is achieved by a special structure on the locker legs 65. There exists a step 66 near the end of both locker legs, which ensures the transverse positioning of the horse-shoe-like locker 64. The step depth is equal to the wall thickness of the housing so that when assembled, the edge of step 66 will stay against the inner wall of the housing. On the other side, two elastically bendable arms 67 and 69 are formed near the other ends of the legs 65 which ensure transverse positioning of the horse-shoe-like locker 64 on that side. The tip 68 of the locking means 60 is constructed such that, when assembled, the edge of tip 68 will stay against the other side of the inner wall of the housing. That transverse locking mechanism ensures horse-shoe-like locker 64 will not drop out as a result of any accidental forces exerted on it. The dimensions of horse-shoe-like locker 64 are such that horse-shoe-like locker 64 is positioned accurately to avoid any contact with shaft tail 34. Details of how the parts of this locking means are related to the housing can further be referenced to FIGS. 7A to 7C Referring to FIGS. 7A to 7C for details of the driven rotor retainer 50 to maintain the driven rotor 40 stays in position under any conditions which would tend to pull it out of open end 29 of transverse passageway 22 of housing 20. The driven rotor 40 is provided with a horse-shoe-like driven rotor retainer 50 that is firmly positioned next to rotor neck 42 of driven rotor 40 by two driven rotor retainer forks 51 through driven rotor retainer slot 24 on the wall of transverse passageway 21 of housing 20. Thus, driven rotor retainer 50 is able to retain rotor head 41 without it dropping out during operation. In addition, there exists a retaining tongue 52 that can be elastically bent between the two retaining forks 51 in driven rotor retainer 50. A retaining hook 53 exists at the tip of retaining tongue 52 that further ensures driven rotor 50 is not dropped out by any accidental forces exerted on it. Two retaining shoulders 54 extends out at the curve side of driven rotor retainer 50 that match the shape of driven rotor retainer slot 24 on the wall of transverse passageway 21 of housing 20. These ensure that driven rotor retainer 50 cannot touch any parts of driven rotor 40 other than rotor head 41.

In order to prevent possible rotational slipping between the prophy cup and the driven rotor during operation, a pair of sharp pointed splinters 46 is arranged circumferentially on the neck of the cup end of the driven gear rotor, upon which the snap-on prophy cup sits. Refer FIG. 2. The splinters 46 pierce into the rubber base of the snap-on prophy cup and force it to rotate with the driven gear rotator without the possible free spinning of the rotor within the prophy cup.

According to above descriptions, a dental prophylaxis angle enclosing in a housing is disclosed. The dental prophylaxis angle comprises a driving shaft engaging and translating a rotational movement to a driven rotor wherein a constant engagement is maintained between the driving shaft and the driven rotor by a first and second position retainers for retaining the driving shaft and the driven rotor at fixed positions respectively. In a preferred embodiment, the first and second position retainers are securely attached to the housing each at a fixed position. In another preferred embodiment, the first position retainer keeping the driving shaft from a horizontal shift and the second position retainers keeping the rotor from a vertical shift. In another preferred embodiment, the housing further having slits for adapting a part of the first and second position retainers for securely keeping the first and second position retainers at fixed positions. In another preferred embodiment, the housing further includes inner steps for mechanically retaining the first and second position retainers for restricting the first and second position retainers from a lateral movement inside the housing. In another preferred embodiment, the housing further includes inner space for adapting a portion of the driven rotor therein for mechanically retaining the rotor from tilting beyond a certain incline angle.

Although the present invention has been described in terms of the presently preferred embodiment, it is to be understood that such disclosure is not to be interpreted as exhaustive or limiting. Various alternations and modifications will no doubt become apparent to those skilled in the art after reading the above disclosure. Accordingly, it is intended that the appended claims be interpreted as covering all alternations and modifications as fall within the true spirit and scope of the invention.

We claim:

1. A disposable dental prophylaxis angle comprising:
   a driving shaft including a gear head, a shaft neck, a shaft shoulder and a shaft tail;
   a driven rotor including a rotor head, a rotor neck, a gear shoulder, a cup flange, a cup neck, and a cup holder;
   a driven rotor retainer having a horse-shoe shape, said rotor retainer connected to said rotor head to ensure that said rotor gear shoulder stays connected to said shaft gear head;
   a driving shaft locking means including a washer and a paw positioner, said shaft locking means locking a shoulder of said shaft tail to ensure said shaft gear head stays connected to said rotor gear shoulder;
   a housing including a longitudinal passageway opening outwardly for coupling with a handpiece and receiving said driving shaft, and a transverse passageway opening outwardly at a right angle to said longitudinal passageway for coupling with a prophy cup and receiving said driven rotor.

2. The dental prophylaxis angle of claim 1, wherein:
   said driving shaft is connected to a handpiece driving end via a tail portion of said driving shaft.

3. The dental prophylaxis angle of claim 1, wherein:
   said shaft having a head portion connected to said driven rotor by a gearing connection, said head portion of said shaft being at an angle, preferably 90 degrees, with respect to said rotor.

4. The dental prophylaxis angle of claim 1, further comprising:
   a driven rotor cup positioner is connected to a prophy cup.

5. The dental prophylaxis angle of claim 1, wherein:
   said driven rotor gear having a shoulder portion connected to said shaft gear head by a gearing connection, said shoulder portion of said driven rotor gear being at an angle, preferably 90 degrees, with respect to said shaft gear head.

6. The dental prophylaxis angle of claim 1, further comprising:
   a mounting and connection section at a confluence of said longitudinal passageway and said transverse passageway, said mounting and connection section providing for a driving connection of said head portion of said shaft and said shoulder portion of said rotor gear.

7. The dental prophylaxis angle of claim 1, wherein:
   said rotor head portion is connected to a positioning hole of said housing in the end of a mounting and connection section in alignment with a central axis of said transverse passageway.

8. The dental prophylaxis angle of claim 1, wherein:
   said rotor head portion is held to said driven rotor retainer at the position of said rotor neck to ensure that said rotor gear shoulder stays connected with said shaft gear head and the diameter of said rotor head being greater than a separation gap of arms of said driven rotor retainer to ensure said driven rotor being held against withdrawal, while the diameter of said rotor neck being smaller than the separation of folks of said driven rotor retainer to ensure small operating friction.

9. The dental prophylaxis angle of claim 7, wherein:
   said mounting and connection section further comprises a mounting slot in said longitudinal passageway where said driven rotor retainer is positioned to mount and retain said driven rotor in a secured position.

10. The dental prophylaxis angle of claim 1, further comprising:
    two axial steps with suitable diameters in said longitudinal passageway to ensure said driving shaft-locking means is firmly and accurately retained for locking said driving shaft.

11. The dental prophylaxis angle of claim 10, wherein:
    said driving shaft locking means comprises a washer and a paw positioner in said longitudinal passageway where said driving shaft locking means is positioned to lock and retain said driving shaft in a secured position to ensure said a gear head of said driving shaft is connected properly with said a gear shoulder of said driven rotor during operation.

12. The dental prophylaxis angle of claim 11, wherein:
    said washer has a hole in alignment with the central axis of longitudinal passageway of said housing and the outer diameter of said washer is greater than the inner diameter of the corresponding step of said housing to ensure in a secure assembly, and said paw positioner being similar to a washer but having several radially extended paws on a surrounding edge, with the outer diameter greater than the inner diameter of a corresponding step of said housing to ensure a more secure assembly to axially locate the said driving shaft.

13. The dental prophylaxis angle of claim 10, wherein:
    said driving shaft locking means comprises a horse-shoe positioner, said horse-shoe positioner having two fork legs perpendicular to the central axis of the longitudinal passageway of said housing, and the separation gap between said fork legs is greater than the diameter of said driving shaft tail, and said horse-shoe positioner is permanently located through a slot and two holes on said housing next to the shoulder of said driving shaft to ensure a secure assembly to axially locate said driving shaft.

14. The dental prophylaxis angle of claim 13, wherein:
    said steps near the end of said fork legs and elastically bent-out branches near a shoe head which ensure the horse-shoe positioner being positioned accurately and securely in both up or down directions on the wall of said housing in the direction perpendicular to the central axis of the longitudinal passageway of said housing.

15. The dental prophylaxis angle of claim 1, wherein:
    said cup holder has a cup holder head and a cup hold neck sized to be forcibly pushed through a retaining hole in said prophy cup, and a cup holder neck having two or more radial splinters to improve an operating engagement with said cup without slipping.

* * * * *